United States Patent
Kong et al.

(10) Patent No.: US 9,173,580 B2
(45) Date of Patent: Nov. 3, 2015

(54) ESTIMATION OF F-WAVE TIMES OF ARRIVAL (TOA) FOR USE IN THE ASSESSMENT OF NEUROMUSCULAR FUNCTION

(75) Inventors: Xuan Kong, Acton, MA (US); Zhixiu Han, Acton, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 918 days.

(21) Appl. No.: 12/074,346

(22) Filed: Mar. 3, 2008

(65) Prior Publication Data
US 2009/0024051 A1    Jan. 22, 2009

Related U.S. Application Data (63) Continuation-in-part of application No. 11/731,271, filed on Mar. 30, 2007, now Pat. No. 8,078,273.

(60) Provisional application No. 60/904,277, filed on Mar. 1, 2007.

(51) Int. Cl.
*A61B 5/04* (2006.01)
*A61B 5/0488* (2006.01)
*A61B 5/00* (2006.01)

(52) U.S. Cl.
CPC ........... *A61B 5/04001* (2013.01); *A61B 5/0488* (2013.01); *A61B 5/7239* (2013.01)

(58) Field of Classification Search
CPC ............ A61B 5/04001; A61B 5/0488; A61B 5/7239; A61B 5/7246
USPC ......................................................... 600/546
See application file for complete search history.

(56) References Cited

U.S. PATENT DOCUMENTS

| | | | | |
|---|---|---|---|---|
| 4,951,266 | A * | 8/1990 | Hsu | 367/25 |
| 5,392,781 | A * | 2/1995 | Phillipps et al. | 600/493 |
| 6,374,140 | B1 * | 4/2002 | Rise | 600/544 |
| 6,665,333 | B2 * | 12/2003 | McCrady et al. | 375/147 |
| 2003/0033140 | A1 * | 2/2003 | Taori et al. | 704/214 |
| 2004/0054479 | A1 * | 3/2004 | Trickett | 702/14 |
| 2006/0025970 | A1 * | 2/2006 | Wegerich | 702/189 |
| 2006/0100540 | A1 * | 5/2006 | Gozani et al. | 600/546 |
| 2006/0217631 | A1 * | 9/2006 | Kong et al. | 600/554 |

\* cited by examiner

*Primary Examiner* — Lee S Cohen
*Assistant Examiner* — Emily Lloyd
(74) *Attorney, Agent, or Firm* — Pandiscio & Pandiscio

(57) ABSTRACT

A method and apparatus for the assessment of neuromuscular function by estimating motor unit F-wave component time of arrival (TOA), comprising: (i) determining and comparing F-wave component features so as to accurately identify individual F-wave components; (ii) repeatedly searching the individual F-wave components and extracting individual F-wavelets from the F-wave components so as to build a complete F-wave TOA profile; and (iii) computing and reporting TOA results for the assessment of neuromuscular function.

31 Claims, 4 Drawing Sheets

F-wave traces, F-wave latencies (solid circles), and F-wavelets

F-wave traces, F-wave latencies (solid circles), and F-wavelets

F-WAVE TRACE AND ITS SAMPLE FEATURES

1  ONE F-WAVE TRACE
2  AMPLITUDE
3  WAVELET DURATION
4  NOISE REGION
5  ACTIVITY REGION
6  QUIET REGION
7  ONSETS
8  ENDS
9  NOISE LEVEL
10 BASELINE

FIG. 4

ESTIMATION OF F-WAVE TIMES OF ARRIVAL (TOA) FOR USE IN THE ASSESSMENT OF NEUROMUSCULAR FUNCTION

REFERENCE TO PENDING PRIOR PATENT APPLICATIONS

This patent application:

(i) claims benefit of prior U.S. Provisional Patent Application Ser. No. 60/904,277, filed Mar. 1, 2007 by Xuan Kong et al. for SINGLE MOTOR UNIT F-RESPONSE TIME OF ARRIVAL; and (ii) is a continuation-in-part of prior U.S. patent application Ser. No. 11/731,271, filed Mar. 30, 2007, now U.S. Pat. No. 8,078,273, by Srivathsan Krishnamachari et al. for DETECTION AND CLASSIFICATION OF NEUROMUSCULAR LATE WAVE ACTIVITY FOR THE ASSESSMENT OF NEUROMUSCULAR FUNCTION.

The above-identified patent application and the above-identified patent are hereby incorporated herein by reference.

FIELD OF THE INVENTION

This invention relates to methods and apparatus for the assessment of neuromuscular functions in general, and more particularly to methods and apparatus for the assessment of neuromuscular functions by more accurately determining the profile of conduction times of the proximal segment of a nerve by estimating the time of arrival of individual F-wave components which together comprise a complete F-wave complex. Traditionally, only the time of arrival of the complete F-wave complex has been considered.

Even more particularly, this invention measures the temporal location, morphology, and similarity of multiple traces of complete F-wave complexes so as to first identify individual F-wave components, in order to thereafter compute the time of arrival of these individual F-wave components.

BACKGROUND OF THE INVENTION

Nerve conduction studies (NCS) play a key role in the assessment of neuropathies, including focal entrapments such as carpal tunnel syndrome and lumbosacral radiculopathies, as well as for neuropathies resulting from diabetes and acquired inflammatory demyelinating polyneuropathies.

NCS are generally conducted by applying an electrical stimulus to a nerve. This electrical stimulation depolarizes a short segment of the nerve (whether a motor nerve or a sensory nerve) at the point of stimulation. If this electrical depolarization exceeds a certain threshold, an action potential impulse is initiated. This action potential impulse propagates along the nerve, both distally and proximally, from the point of stimulation.

In the case of a motor nerve, distally-propagating nerve impulses reach the muscle and depolarize the muscle fibers, typically causing a response or "twitch" in that muscle. This electrical activity of the muscle is measured as a compound muscle action potential (CMAP).

Proximally-propagating impulses reach the motor neuron cell bodies located in the anterior horn of the spinal cord. In a small, and random, fraction of the stimulated neurons, the neuron depolarizes again (i.e., it "backfires"), resulting in a new distally-traveling impulse (this is sometimes referred to as "back propagation"). The muscle responses resulting from these back-propagating impulses are generally referred to as F-waves.

F-waves travel through a longer segment of the nerve than CMAPs and are therefore more sensitive to systemic changes in the conduction properties of the nerve fibers and/or localized changes in the proximal segment of the nerve fibers. F-waves have been routinely used as a clinical measurement to provide useful diagnostic information in the evaluation of neuromuscular function and neuropathies.

Figure 1:
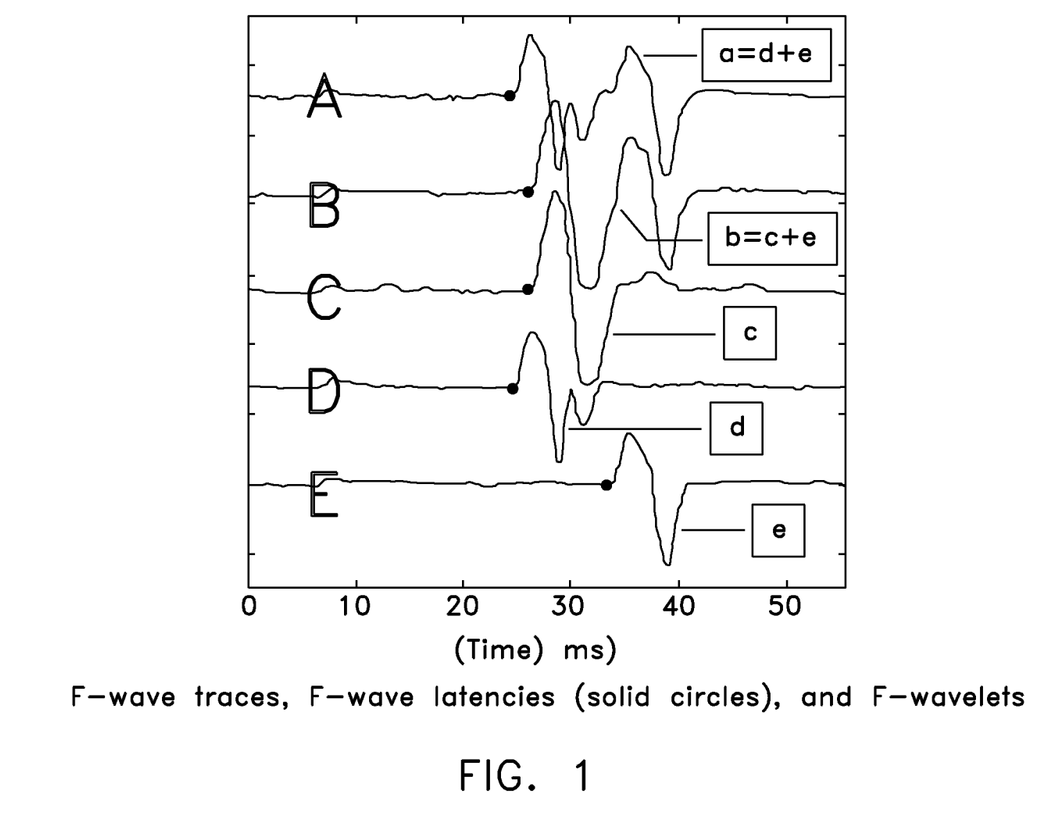
FIG. 1 illustrates a plurality of F-wave traces, with their associated F-wave latencies and their constituent F-wavelets.

The recorded muscle activities which result from an electrical stimulus are generally referred to as a response trace. The temporal segment of the response trace, which corresponds to the time frame of possible F-wave activities, is called an F-wave trace. FIG. 1 shows a set of five F-wave traces, marked as trace A through trace E.

Current approaches for using F-waves to evaluate neuromuscular function generally identify the time of the earliest F-wave activity in each trace (denoted as solid dots in FIG. 1), and define the onset time of this earliest F-wave activity, which is also known as the F-wave latency (FWL). For a given group of F-wave traces, the minimum, average and maximum FWL values (i.e., times) are calculated for that group of F-wave traces and defined to be the minimum FWL, the mean FWL and the maximum FWL parameters for that group of F-wave traces, respectively. These and other FWL parameters, such as F-wave persistence and chronodispersion, are frequently used by clinicians for multiple clinical applications. These clinical applications include (i) the detection of lumbosacral radiculopathy; (ii) the detection of dynamic changes associated with lumbar spinal stenosis; (iii) the early detection of axonal and demyelinating polyneuropathies; (iv) the demonstration of therapeutic response of pharmacological agents such as baclofen; and (v) the monitoring of changes in the motor neuron pool and central nervous system. Thus, determining FWL is frequently of significant interest to the clinician looking to assess neuromuscular function and/or treat neuropathies.

Another F-wave parameter which can be used to assess neuromuscular function is the time of arrival (TOA) of the F-wave components (F-wavelets). Each backfiring motor neuron produces a nerve impulse traveling along its own nerve fibers (i.e., its axons) before reaching the muscle fibers of the muscle group which is to be studied. The propagation time of each nerve impulse determines the TOA of an F-wavelet (a component of a complete F-wave complex) that may vary according to variations in axonal conduction velocity. For example, conduction velocity may vary due to partial or incomplete injury that affects only some, but not all, axons.

For any given stimulus, when only one motor neuron backfires, or when a few motor neurons backfire but they all have relatively close conduction speeds, one F-wavelet (with only one determinable TOA) may be formed. See, for example, FIG. 1, where F-wave traces C, D and E contain a single F-wavelet c, d and e, respectively.

However, when several motor neurons backfire with different conduction speeds, multiple F-wavelets may appear and form a complex F-wave response. See, for example, FIG. 1, where the F-wave trace A contains two distinct F-wavelets, a=d+e, and only the earliest TOA (i.e., the TOA of F-wavelet d) defines the FWL for the whole F-wave (i.e., the FWL of the complete F-wave complex in trace A). Similarly, and still looking at FIG. 1, F-wave trace B contains two distinct F-wavelets, b=c+e, and only the earliest TOA (i.e., the TOA of F-wavelet c) defines the FWL for the whole F-wave (i.e., the FWL of the complete F-wave complex in trace B).

If only FWL is considered, any clinically relevant TOA information contained in later F-wavelets (e.g., the TOA of F-wavelet e in trace A, and the TOA of F-wavelet e in trace B) is effectively lost. This essentially creates a masking effect with respect to the TOA of the later F-wavelets, and hence reduces the F-wave diagnostic sensitivity. One example where such a masking effect results in reduced sensitivity is in the detection of lumbosacral radiculopathies.

Due to the difficulties in accurately determining the TOA of the later F-wavelets in a complete F-wave complex, clinical F-wave analyses have traditionally relied heavily on FWL, and minimized reliance on TOA.

In addition to aforementioned complexities associated with clinical F-waves analyses, and particularly with using clinical F-waves analyses based on TOA, F-waves also exhibit other characteristics which can complicate their use in clinical assessment and analyses. For example, when compared to CMAPs, F-waves appear to have a highly variable morphology and a very low amplitude due to the small and random number of neurons backfiring at any given time. The acquired F-wave signals also contain noise, power-line frequency interference (PFI) and baseline disturbances.

Thus, there is a need for an automated method to accurately identify and extract individual F-wavelets from a complete F-wave complex, determine the TOA for each F-wavelet, and thereafter construct a TOA profile for the patient nerve based on the TOAs of the specific F-wavelets.

SUMMARY OF THE INVENTION

As noted above, the F-wave activity observed in each F-wave trace is generally the result of activity components generated by multiple, randomly-firing motor neurons. This F-wave activity typically comprises one or more F-wavelets within the complete F-wave complex of a trace. The present invention provides a novel method and apparatus to identify and extract individual F-wavelets from the F-wave traces. The extraction of such F-wavelets then permits a TOA profile of the specific F-wavelets to be created, which in turn permits the creation of a complete nerve conduction profile for the nerve fibers under study.

In other words, the present invention provides an automated system for analyzing F-waves and extracting individual F-wavelets from a complete F-wave complex. This system applies signal processing techniques in order to decompose F-wave traces into their constituent components. These F-wave components are then used to construct a TOA profile for the patient nerve. This TOA profile can then be used clinically to assess neuromuscular function and/or diagnose neuropathy.

Thus it will be seen that the present invention provides an automated system for accurately identifying and extracting individual F-wavelets from a complete F-wave complex, determining the TOA for each F-wavelet, and thereafter constructing a TOA profile for the patient nerve based on the TOAs of the various F-wavelets.

In accordance with the present invention, there is provided a method for (1) detecting F-wave activities (i.e., specific features of an F-wave trace) and, using those detected activities, (2) decomposing the F-wave trace into individual F-wave components using an automated process. In one preferred form of the present invention, this method comprises the following steps:

(1) F-Wave Features Calculation. Specific features of each F-wave trace, such as amplitude, activity region, quiet region, onset, ends and durations, are pre-calculated so as to be used in the following step of decomposing each F-wave trace into specific F-wavelets.

(2) F-wave Decomposition. F-wavelets that occur in different F-wave traces have been shown to have similar features and morphology. These F-wave components may be identified and then extracted by (i) comparing the previously-determined features of the F-waves, and (ii) measuring the similarity of the waveforms so as to identify individual F-wave components within the F-wave trace (i.e., within the complete F-wave complex).

With the F-wave features calculated and the F-wave decomposed into its constituent F-wavelets, the TOA of each individual F-wavelet can thereafter be calculated. Once the TOAs of the individual F-wavelets are established, the TOAs can then be used in ways well known in the art to assess neuromuscular function and/or to diagnose neuropathy.

The aforementioned steps are preferably performed using a general purpose computer provided with appropriate programming, and/or with a dedicated computer provided with appropriate programming, in a manner which will be apparent to those skilled in the art in view of the present disclosure.

The aforementioned F-wave features calculation and decomposition steps will hereinafter be discussed in greater detail.

(1) F-Wave Features Calculation. Each F-wave trace is examined individually. The F-wave activity temporal segment and onset are preferably pre-determined using the automated algorithms disclosed in pending prior U.S. patent application Ser. No. 11/731,271, filed Mar. 30, 2007 by Srivathsan Krishnamachari et al. for DETECTION AND CLASSIFICATION OF NEUROMUSCULAR LATE WAVE ACTIVITY FOR THE ASSESSMENT OF NEUROMUSCULAR FUNCTION, which patent application is hereby incorporated herein by reference. Other important features such as noise, quiet regions, activity regions, amplitudes, ends and durations are also calculated as described below.

(1a) F-wave Trace Noise Level. The F-wave trace noise level is determined from the F-wave signal noise region. The F-wave signal noise region is defined to be the portion of an F-wave trace which is between the trace start and the onset of F-wave activity. The noise level in this region (i.e., the F-wave signal noise level) is estimated on a trace-to-trace basis and is used in the calculation of F-wave features.

(1b) F-wave Activity Region. F-wave activity regions are used to define F-wave activities and describe an F-wave temporal location, such that the main activities of the F-wave can be used in later-applied similarity measurements. An F-wave activity region is calculated to meet several pre-determined criteria, including an amplitude threshold, a length threshold and a slope threshold.

(1c) F-wave Quiet Region. The F-wave quiet region is defined to be the portion of an F-wave trace that contains no measurable neuromuscular activity (and is between individual F-wave components). The quiet region provides the opportunity to later separate an F-wave trace into its constituent F-wave components. Like the activity region, the quiet region is calculated to meet specific, pre-determined criteria including a length threshold and an amplitude threshold.

(1d) Ends And Durations. An F-wave end indicates the ending point of an F-wave component. It is found at the end of an activity region of an F-wave. In other words, the end is determined as the last point of an activity region, and at this end point, the signal amplitude and slope both meet pre-set thresholds. The duration of an F-wave component is defined to be the calculated time distance between the onset of the F-wave component and the end of the F-wave component.

(1e) Similarity Measurement. Similar F-wave components may occur in different F-wave traces. The corresponding F-wave components exhibit a similar morphology and occur on a very close temporal segment in the traces. A similarity measurement is provided in order to identify such repeated F-wave components across the multiple traces. By way of example but not limitation, the similarity measurement may be determined using the Normalized Cross-Correlation (NCC) method, the Pseudo-correlation (PsC) method and/or the Normalized Euclidian Distance (NED) measurement method.

(2) Decomposition. An F-wave trace may contain more than one F-wave components. Decomposition of the F-wave trace identifies all of the individual F-wave components present in the complete F-wave complex. The identified individual F-wave components can then be used to build a TOA profile of the complete F-wave. This TOA profile can then be used for the better assessment of neuromuscular function.

F-wave features and their associated waveform similarities are compared with one another in order to decompose the F-waves into individual F-wavelets. By way of example but not limitation, and in order to avoid incorrect or inaccurate extraction of F-wavelets, the present invention identifies three conditions and requires that at least one of these three conditions be met in order to proceed with automated F-wave decomposition. In other words, in accordance with the present invention, automated F-wave decomposition into individual F-wavelets proceeds (i) only when one or more of the following conditions is met, and (ii) in accordance with the decomposition procedure appropriate with that condition:

Condition I. A long F-wave has a quiet region between its F-wave components, and this quiet segment satisfies a pre-set criteria.

In this case, the long complex F-wave is separated into individual components at the middle of the quiet region.

Condition II. A complex F-wave is identical to the superimposition of two or more existing F-wave components.

In this case, the complex F-wave is decomposed into these F-wave components.

Condition III. A long complex F-wave has one portion (either an earlier segment or a later segment) similar to an existing short F-wave component of a different trace and, after subtracting the short existing wave component from the long complex F-wave, the onset of the residual wave component (when the earlier portion is similar to the short F-wave component), or the end of the residual wave component (when the later portion is similar to the short F-wave component), is shifted by a meaningful amount that meets a pre-set threshold.

In this case, the complex F-wave is separated into two individual F-wave components, i.e., the short F-wave components and the residual wave components.

Thus, if one or more of the preceding conditions is met, automated F-wave decomposition proceeds so as to decompose the F-wave trace into individual F-wave components. As will hereinafter be discussed in further detail below, F-wave features and their associated waveform similarities are compared with one another in order to decompose the F-waves into individual F-wavelets.

In one preferred form of the present invention, there is provided a method for the assessment of neuromuscular function of an individual, the method comprising the steps of:

stimulating a nerve so as to create a plurality of F-wave traces;

identifying specific waveform features of the F-wave traces;

using the identified waveform features to identify all F-wavelets contained within the F-wave traces;

estimating a time of arrival (TOA) for each F-wavelet contained within the F-wave traces;

creating a TOA profile for the nerve using the TOA of each F-wavelet contained within the F-wave traces; and using the TOA profiles of one or more nerves to assess neuromuscular function of the individual.

In another preferred form of the present invention, there is provided a method for identifying each of the constituent F-wavelets contained within an F-wave trace, the method comprising the steps of:

identifying specific waveform features of the F-wave trace;

identifying F-wave components within the F-wave trace, wherein the F-wave components comprise activity regions separated by quiet regions;

identifying each F-wave component within the F-wave trace by comparing the component with at least one F-wavelet of at least one other F-wave trace and calculating a similarity measurement for that F-wave component;

for each F-wave component having a similarity measurement which does not meet a pre-determined criteria, defining the F-wave component as constituting a single F-wavelet, and for each F-wave component having a similarity measurement which meets a pre-determined criteria, defining the F-wave component as constituting more than one F-wavelet; and for each F-wave component defined to constitute more than one F-wavelet, decomposing that F-wave component into its constituent F-wavelets based on the similarity measure.

In another preferred form of the present invention, there is provided a method for creating an F-wave TOA profile for a nerve, the method comprising the steps of:

stimulating a nerve so as to create a plurality of F-wave traces;

identifying specific waveform features of the F-wave traces;

using the identified waveform features, identifying individual F-wave components within an F-wave trace, wherein the F-wave components comprise activity regions separated by quiet regions;

comparing the F-wave components within a specific F-wave trace with the at least one F-wave component of at least one other F-wave trace and calculating a similarity measurement for that F-wave component;

for each F-wave component having a similarity measurement which does not meet a pre-determined criteria, defining the F-wave component as constituting a single F-wavelet, and for each F-wave component having a similarity measurement which meets a pre-determined criteria, defining the F-wave component as constituting more than one F-wavelet;

for each F-wave component examined and determined to constitute more than one F-wavelet, decomposing that F-wave component into its constituent F-wavelets;

repeating the foregoing process until all possible decomposition has been effected, and then defining each of the remaining F-wave components as an F-wavelet;

estimating the time of arrival (TOA) of each F-wavelet contained within the specific F-wave trace; and creating a TOA profile for the nerve using the estimated TOAs from one or more F-wave traces.

In another preferred form of the present invention, there is provided apparatus for the assessment of neuromuscular function of an individual, the apparatus comprising the steps of:

apparatus for stimulating a nerve so as to create a plurality of F-wave traces;

apparatus for identifying specific waveform features of the F-wave traces;

apparatus for using the identified waveform features to identify all F-wavelets contained within the F-wave traces;

apparatus for estimating a time of arrival (TOA) for each F-wavelet contained within the F-wave traces;

apparatus for creating a TOA profile for the nerve using the TOA of each F-wavelet contained within the F-wave traces; and apparatus for using the TOA profiles of one or more nerves to assess neuromuscular function of the individual.

In another preferred form of the present invention, there is provided apparatus for identifying each of the constituent F-wavelets contained within an F-wave trace, the apparatus comprising the steps of:

apparatus for identifying specific waveform features of the F-wave trace;

apparatus for identifying F-wave components within the F-wave trace, wherein the F-wave components comprise activity regions separated by quiet regions;

apparatus for identifying each F-wave component within the F-wave trace by comparing the component with at least one F-wavelet of at least one other F-wave trace and calculating a similarity measurement for that F-wave component and, for each F-wave component having a similarity measurement which does not meet a pre-determined criteria, defining the F-wave component as constituting a single F-wavelet, and for each F-wave component having a similarity measurement which meets a pre-determined criteria, defining the F-wave component as constituting more than one F-wavelet and, for each F-wave component defined to constitute more than one F-wavelet, decomposing that F-wave component into its constituent F-wavelets based on the similarity measurement.

In another preferred form of the present invention, there is provided apparatus for creating an F-wave TOA profile for a nerve, the apparatus comprising the steps of:

apparatus for stimulating a nerve so as to create a plurality of F-wave traces;

apparatus for identifying specific waveform features of the F-wave traces;

apparatus for using the identified waveform features, and identifying individual F-wave components within an F-wave trace, wherein the F-wave components comprise activity regions separated by quiet regions;

apparatus for comparing the F-wave components within a specific F-wave trace with the at least one F-wave component of at least one other F-wave trace and calculating a similarity measurement for that F-wave component;

the apparatus, for each F-wave component having a similarity measurement which does not meet a pre-determined criteria, defining the F-wave component as constituting a single F-wavelet, and for each F-wave component having a similarity measurement which meets a pre-determined criteria, defining the F-wave component as constituting more than one F-wavelet and, the apparatus, for each F-wave component examined and determined to constitute more than one F-wavelet, decomposing that F-wave component into its constituent F-wavelets;

the apparatus repeating the foregoing process until all possible decomposition has been effected, and then defining each of the remaining F-wave components as an F-wavelet;

apparatus for estimating the time of arrival (TOA) of each F-wavelet contained within the specific F-wave trace; and apparatus for creating a TOA profile for the nerve using the estimated TOAs from one or more F-wave traces.

In another preferred form of the present invention, there is provided a method for the assessment of neuromuscular function of a person, the method comprising the steps of:

stimulating a nerve so as to create a plurality of F-wave traces;

identifying specific waveform features of the F-wave traces;

using the identified waveform features to identify all F-wave components contained within the F-wave traces;

estimating a time of arrival (TOA) for each F-wave component contained within the F-wave traces;

creating a TOA profile for the patient nerve using the TOA of each F-wave component contained within the F-wave traces; and using the TOA profile of the person's nerve to assess neuromuscular function of the person.

In another preferred form of the present invention, there is provided a method for identifying each of the constituent F-wave components contained within an F-wave trace, the method comprising the steps of:

identifying specific waveform features of the F-wave trace;

identifying F-wave components within the F-wave trace, wherein the F-wave components comprise activity regions separated by quiet regions;

identifying F-wave components from an F-wavelet complex within the F-wave trace by comparing that F-wavelet complex with at least one F-wave component of at least one other F-wave trace and calculating a similarity measurement for that F-wavelet complex with respect to the compared F-wave component;

for each F-wavelet complex having a similarity measurement which does not meet a pre-determined criteria, defining the F-wavelet complex as constituting a single F-wave component, and for each F-wavelet complex having a similarity measurement which meets a pre-determined criteria, examining the F-wavelet complex as if constituting more than one F-wave component; and for each F-wavelet complex verified to constitute more than one F-wave component, decomposing that F-wavelet complex into its constituent F-wave components.

In another preferred form of the present invention, there is provided a method for creating an F-wave TOA profile for a person's nerve, the method comprising the steps of:

stimulating a nerve so as to create a plurality of F-wave traces;

identifying specific waveform features of the F-wave traces;

using the identified waveform features, identifying individual F-wave components within an F-wave trace, wherein the F-wave components comprise activity regions separated by quiet regions;

comparing the F-wavelet complex within a specific F-wave trace with at least one F-wave component of at least one other F-wave trace and calculating a similarity measurement for that F-wavelet complex;

for each F-wavelet complex having a similarity measurement which does not meet a pre-determined criteria, defining the F-wavelet complex as constituting a single F-wave component; and for each F-wavelet complex having a similarity measurement which meets a pre-determined criteria, examining the F-wavelet complex as if constituting more than one F-wave component;

for each F-wavelet complex examined and verified to constitute more than one F-wave component, decomposing that F-wavelet complex into its constituent F-wave components;

treating each extracted F-wave component as a new F-wavelet complex, and applying the foregoing steps recursively until all decomposition has been effected, and then defining each of the resulting F-wave components as an F-wave component;

estimating the time of arrival (TOA) of each F-wave component contained within the specific F-wave trace; and creating a TOA profile for the person's nerve using the estimated TOAs.

The present invention will be further understood upon consideration of the following detailed description, drawings and claims.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention provides an automated method and apparatus to determine the TOA of individual F-wavelets in order to construct a TOA profile for the patient nerve which can then be used for the assessment of neuromuscular function. Furthermore, the method and apparatus of the present invention unmasks (i.e., identifies) individual F-wavelets within a complete F-wave complex, and is capable of building a better conduction velocity profile of the nerve fibers under study for the more accurate and reliable diagnosis of neuropathies.

Figure 2:
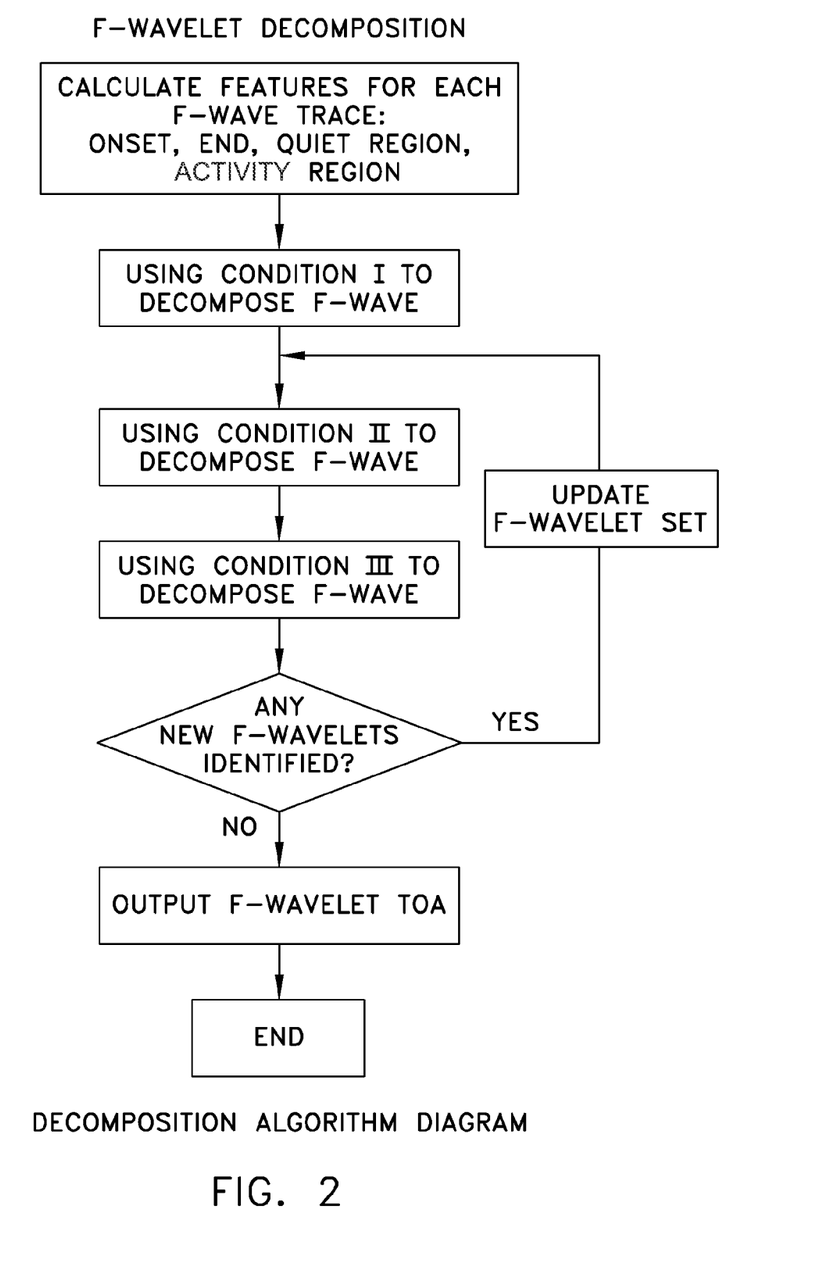
FIG. 2 illustrates, in the form of a top-level flow chart, the preferred methodologies of the present invention.

A preferred methodology for the present invention is illustrated in FIG. 2 and comprises the following steps:

(1) F-Wave Feature Calculations. An F-wave trace may contain up to several F-wave components, each associated with a backfiring motor neuron. These motor neuron F-wave components may appear on the trace as distinct individual wavelets, or they may appear to be coupled together so as to form a wavelet complex with a highly variable morphology. For example, and looking next at FIG. 3, there is shown an exemplary F-wave trace 1 comprising two distinct F-wave components. The first F-wave component (shown in the earlier portion of the trace, i.e., on the left hand side of the trace) could be a combination of two motor neuron responses. The second F-wave component (shown in the later portion of the trace, i.e., the right hand side of the trace) may be a single motor neuron response.

The concept of separating the first F-wave component from the second F-wave component, and further separating a particular F-wave component into one or more constituent F-wave components, may appear simple, however, given the complexity of the waveforms, it can be difficult to achieve this accurately with an automated algorithm. For example, in order to identify, separate and extract individual motor neuron responses from the first F-wave component shown in FIG. 3, the F-wave features and morphology must first be calculated and compared to F-wave features of other F-wave traces. Based on this comparison, if the first F-wave component can be verified as identical to the superimposition of other F-wave components, then it will be broken into individual F-wave components for later TOA calculation. However, if the first F-wave component cannot be verified as identical to the superimposition of other F-wave components of other traces, the first F-wave component is considered to be a single F-wave component for later TOA calculation.

Each F-wave component (for example, the first wave component in FIG. 3) can be described by its amplitude 2, onset 7, end 8, wavelet duration 3, activity regions 5, and morphology. Amplitude 2 is defined as the distance between the most positive peak and most negative peak in the waveform. Wavelet duration 3 is defined as the point of initial departure from the baseline 10 (i.e., the onset 7) to the point of final return to the baseline 10 (i.e., the end 8). Activity regions 5 are defined as the portions of a potential between the baseline departure and the baseline return. Quiet region 6 is defined as a segment between separate F-wave components.

Figure 3:
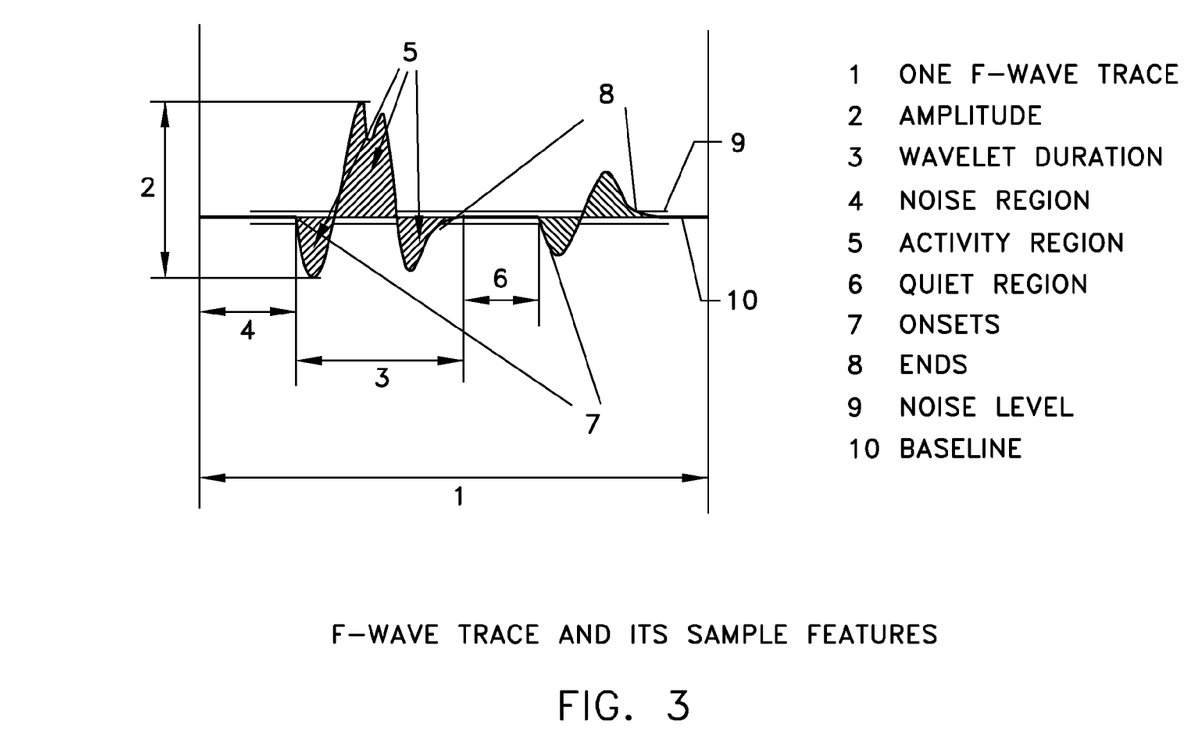
FIG. 3 illustrates an F-wave trace and its associated features.

In the calculation of F-wave features, each F-wave component of each F-wave trace is examined individually. The F-wave temporal segment and onset are preferably pre-determined using the automated algorithm disclosed in pending prior U.S. patent application Ser. No. 11/731,271, filed Mar. 30, 2007 by Srivathsan Krishnamachari et al. for DETECTION AND CLASSIFICATION OF NEUROMUSCULAR LATE WAVE ACTIVITY FOR THE ASSESSMENT OF NEUROMUSCULAR FUNCTION, which patent application is hereby incorporated herein by reference. Some other important F-wave component features include noise level 9, quiet region 6, wavelet ends 8 and activity regions 5, and may also be calculated as will hereinafter be described.

(1a) F-wave Trace Noise Level. The noise level of an F-wave is estimated on a trace-by-trace basis and is thereafter used to calculate F-wave features. The signal noise region 4 of the F-wave is considered to be the portion of the F-wave trace which is between the start of the F-wave trace and the point of F-wave onset (in other words, the point where F-wave activity is first detected). The noise RMS (root mean square) value, and its derivative RMS value, are calculated so as to define this noise level.

(1b) F-wave Activity Regions. F-wave activity regions are used to better describe the main activity portions of a given F-wave, so that the main portion of an F-wave can be properly identified and the aforementioned similarity measurement can be more accurately applied.

F-wave activity regions are defined to be the trace segments having an amplitude greater than 3 times the noise RMS value. In addition to having an amplitude at least three times the noise RMS value, an F-wave activity region must also meet all three of the following criteria:

(i) the regional maximum peak value must be larger than a pre-set threshold, for example, the pre-set threshold may be set at $\frac{1}{9}$ of the overall F-wave complex amplitude;

(ii) the regional segment length must be longer than a pre-set threshold, for example, the threshold may be set at $\frac{1}{6}$ of the median value of the peak-to-peak distance on a time scale for all F-wave traces; and (iii) the maximum derivative value must be greater than 3 times the noise derivative RMS value. This threshold must be met in order to exclude flat segments.

(1c) Quiet Region. The quiet region is defined as a segment between F-wave components which contains no nerve activities. The quiet region is also defined as meeting a pre-set threshold, for example, the threshold may be set at one or both of the following conditions:

(i) a segment that is at least 2.5 ms long, and within that segment, both the signal and signal derivative values are less than twice the noise RMS value and noise derivative RMS values, respectively; or (ii) a segment that is longer than 5 ms and contains a period of more than 4 ms total in which either the signal or the signal derivative value is less than twice the noise RMS value or noise derivative RMS value, respectively.

(1d) Ends And Durations. The end of an F-wave component is located at the end of an activity region of an F-wave. In other words, the end is determined as the last point of the activity region and, at this end point, the signal derivative is larger than twice the noise derivative RMS value, or the signal value is larger than 4 times the noise RMS value.

It should be noted that the end point is not the point of return to the baseline 10, however, the end point can be used to better, define the main activity of the F-wave component because, in most cases, F-waves return to the baseline very slowly in their ending sections.

The F-wave component duration is the calculated time difference between the onset of the F-wave component and the end of the F-wave component.

(1e) Similarity Measurement. To measure the similarity between various F-wave components, several methods have been investigated and tested, including the NCC method, the PsC method and the NED measurement method. Based on a comparison study of these three methods, PsC is generally preferred because it has been found to have the highest sensitivity and specificity in signal comparison.

The PsC method is defined as follows:

For two given signals $\vec{x}$ and $\vec{y}$, $\{x_i, y_j, i=1, \ldots, m; j=1, \ldots, n; m \le n\}$, its PsC is defined as $$PsC_k = \max\left\{\frac{\sum_{i=1}^{m}(x_i y_{k+i} - |x_i - y_{k+i}|\max\{|x_i|, |y_{k+i}|\})}{\sum_{i=1}^{m}(\max\{|x_i|, |y_{k+i}|\})^2}, 0\right\}, k = 0, 1, \ldots, l.$$

Here, the PsC vector holds similarity values at different lags k of signal x with respect to signal y. PsC values range from 0 (i.e., indicating little similarity) to 1 (i.e., indicating highest similarity, or a "perfect match").

As will hereinafter be discussed, the similarity measurement is used to determine whether an F-wave component should be decomposed into constituent F-wave components.

(2) Decomposition. The decomposition algorithm is used to determine whether a given F-wave comprises constituent F-wave components and, if so, separates the F-wave into those constituent F-wave components. Due to the complexity of F-wave morphology, the decomposition algorithm used in the preferred embodiment of the present invention is designed to use a conservative approach, such that only identifiable (i.e., true) motor neuron responses are extracted as F-wave components.

Figure 4:
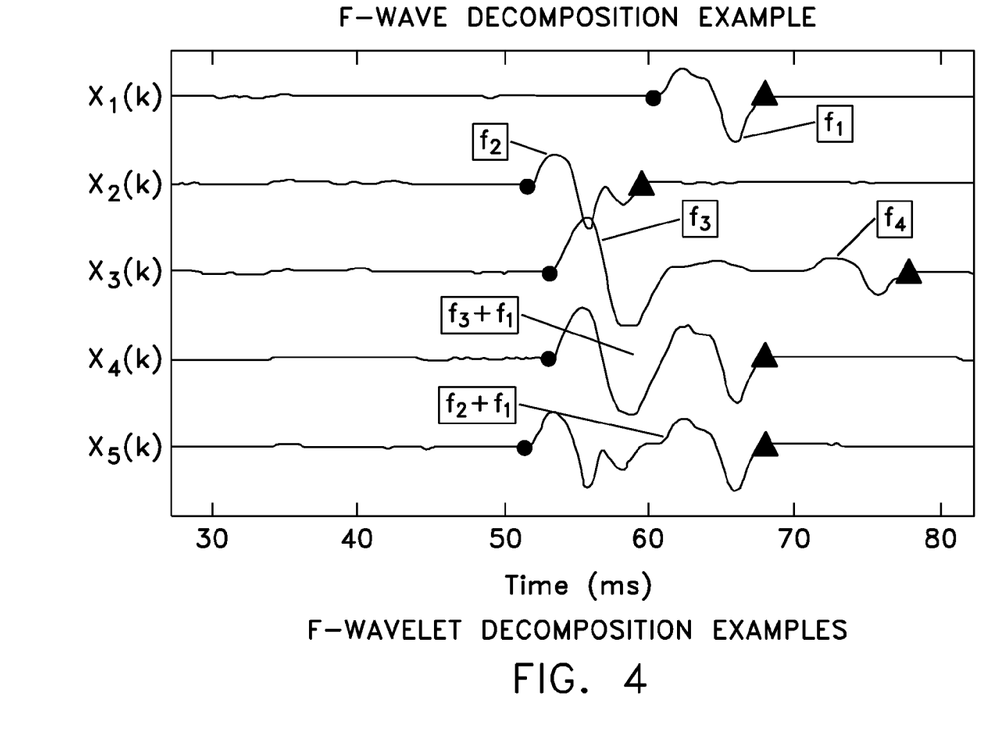
FIG. 4 illustrates an exemplary F-wave decomposition into its constituent individual F-wave components.

The decomposition approach can be illustrated by looking at the example of FIG. 4. More particularly, waveforms $X_1$, $X_2$, $X_3$, $X_4$ and $X_5$ represent five different F-wave traces. $X_1$ contains one F-wave component $f_1$; $X_2$ contains another F-wave component $f_2$; $X_3$ contains two F-wave components which are $f_3$ (the first F-wave component) and $f_4$ (the second F-wave component); $X_4$ contains two F-wave components which are repeaters of $f_3$ and $f_1$, respectively; and $X_5$ contains two F-wave components which are also repeaters, but are of $f_2$ and $f_1$, respectively.

The preferred decomposition approach can be described as follows:

(2a) Calculate F-wave Features. First, automated algorithms are used to determine the TOA of the earliest F-wave component (i.e., the TOAs marked in FIG. 4 as solid dots) and the end of the last F-wave component (i.e., the ends marked in FIG. 4 as triangles) for each of the F-wave traces. A quiet region between F-wave component $f_3$ and F-wave component $f_4$ in F-wave trace $X_3$ is also identified.

As noted above, an F-wave trace may contain more than one F-wave component. Decomposition of the F-wave trace identifies all of the individual F-wave components present in a given F-wave trace. The identified individual F-wave components can then be used to build a TOA profile. This TOA profile can then be used for the better assessment of neuromuscular function.

F-wave features and their associated waveform similarities are compared with one another in order to decompose the F-waves, into individual F-wave components. By way of example but not limitation, and in order to avoid incorrect or inaccurate extraction of F-wave components, the present invention identifies three conditions and requires that at least one of the these three conditions be met in order to proceed with automated F-wave decomposition in accordance with the present invention. In other words, automated F-wave decomposition into individual F-wave components proceeds (i) only when one or more of the following conditions are met, and (ii) in accordance with the decomposition procedure appropriate with that condition:

Condition I. A F-wave trace has one or more quiet regions between the F-wave components, and the quiet segments satisfy a pre-set criteria.

In this case, the long complex F-wave is separated into individual components at the middle of the quiet region.

In the example shown in FIG. 4, F-wave trace $X_3$ has a quiet region between F-wave components $f_3$ and $f_4$, and the quiet region is longer than the pre-set threshold. Thus, the F-wave components $f_3$ and $f_4$ are separated and identified as two independent F-wave components.

Condition II. A complex F-wave is identical to the superimposition of two or more existing F-wave components. Here, "identical" is intended to mean that two components have a similar onset, end and amplitude, and also meet a pre-set similarity measure.

In such a case, the complex F-wave is decomposed into two separate F-wave components.

In the example shown in FIG. 4, F-wave trace $X_5$ is identical to the superimposition of F-wave components $f_1$ and $f_2$, and thus F-wave trace $X_5$ is decomposed into two components $f_1$ and $f_2$.

Condition III. A long complex F-wave has one portion (either an earlier segment or a later segment) similar to an existing short F-wave component (of a different trace) and, after subtracting the existing short wave component from the long complex F-wave, the onset of the residual wave component (when the earlier portion is similar to the short F-wave component), or the end of the residual wave component (when the later portion is similar to the short F-wave component), is shifted by a meaningful amount that meets a pre-set length threshold.

In this case, the long complex F-wave is separated into two individual F-wave components, i.e., the short F-wave component and the residual wave component.

In the example shown in FIG. 4, the later portion of F-wave trace $X_4$ is similar to F-wave component $f_1$ (i.e., the later portion meets a similarity measure at the temporal location from onset to end of F-wave component $f_1$), and after subtracting $f_1$ from $X_4$, the end point of the residual wave component has shifted by a significant amount, and that meets a shift threshold. Thus, this long complex F-wave trace $X_4$ is separated into two separate individual F-wave components. In essence, the residual wave component is identical to the extracted wave component $f_3$ (from step 2b). If the residual wave component and the extracted wave component are not identical, this decomposition is still accepted because the end shift meets the pre-set threshold.

The above process may be repeated with newly extracted F-wave components so as to extract further constituent F-wave components, until all constituent F-wave components have been identified and extracted.

Once all individual F-wave components have been extracted from an F-wave, the TOA of each F-wave component can be identified. From this, a TOA profile can be constructed for the nerve based on the TOAs of all F-wave components (F-wavelets). The TOA profile can be used in the assessment of neuromuscular function and/or diagnosis and treatment of neuropathy.

Thus it will be seen that this invention discloses a method and apparatus for estimating motor F-wavelet time of arrival (TOA). The method and apparatus of the present invention calculate F-wave features, such as activity region, quiet region, onset, end, amplitude, etc. An automated algorithm is provided to compare, identify and extract individual F-wavelets from the F-wave traces, and report F-wavelet TOAs which can thereafter be used to construct a TOA profile which can be used clinically so as to assess neuromuscular function.

In other words, a person has multiple nerves. For each nerve, a TOA profile can be created, and generally multiple nerves (and thus multiple TOA profiles for these nerves) can be used to assess the person's neuromuscular function and/or diagnose neuropathy. Each nerve can be stimulated multiple times in order to obtain multiple F-wave traces. Each F-wave trace may contain one or more F-wavelets, and a TOA can be defined with respect to each F-wavelet. Each F-wave trace may contain one or more F-wave components (which can be viewed as an intermediate product), and each F-wave component may contain one or more F-wavelets (which can be viewed as the final product). Similar F-wavelets and/or F-wave components may appear in more than one F-wave trace. Similarity can be defined for F-wave components and F-wavelets. This similarity can be used during a decomposition process to decompose a complex F-wave trace into one or more F-wave components, which in turn further decomposed into one or more constituent F-wavelets.

Pre-Processing the F-Wave Traces in Order to Improve Feature Calculation and Decomposition The present invention involves the analysis and decomposition of F-wave traces. It will be appreciated that the purity of the F-wave trace can affect the accuracy of the analysis and decomposition. As noted above, F-waves can be difficult to analyze manually or with automation, since they generally have a very low amplitude (due to the small of random number of neurons backfiring at any given time), noise, power-line frequency interference (PFI) and baseline disturbances. Therefore, it can be helpful to pre-process the F-wave traces so as to remove noise, PFI, baseline components and/or other artifacts before conducting the aforementioned steps of feature calculation and decomposition. This can be done using the automation algorithms disclosed in pending prior U.S. patent application Ser. No. 11/731,271, filed Mar. 30, 2007 by Srivathsan Krishnamachari et al. for DETECTION AND CLASSIFICATION OF NEUROMUSCULAR LATE WAVE ACTIVITY FOR THE ASSESSMENT OF NEUROMUSCULAR FUNCTION, which patent application is hereby incorporated herein by reference.

Operations in Domains Other than the Time Domain

In the foregoing discussion of the present invention operations were conducted in the time domain. However, it is also possible to conduct the operations of the present invention in other domains, e.g., the time-frequency domain (where F-wave decomposition is conducted in the frequency domain and F-wave TOAs are estimated in the time domain). Such domains may generally be referred to as transform domains.

Modifications of the Preferred Embodiments

It will be appreciated that still further embodiments of the present invention will be apparent to those skilled in the art in view of the present disclosure. It is to be understood that the present invention is by no means limited to the particular constructions and method steps herein disclosed and/or shown in the drawings, but also comprises any modifications or equivalents within the scope of the invention.

What is claimed is:

1. A method for the assessment of neuromuscular function of an individual, the method comprising the steps of using a computer to:
   electrically stimulate a nerve so as to create a plurality of F-wave traces;
   identify specific waveform features of each of the plurality of F-wave traces;
   use the identified waveform features to identify all F-wavelets contained within the plurality of F-wave traces;
   estimate a time of arrival (TOA) for each F-wavelet contained within the plurality of F-wave traces;
   create a TOA profile for the nerve using the estimated TOA of each F-wavelet contained within the plurality of F-wave traces; and
   use the TOA profile of the nerve to assess neuromuscular function of the individual.

2. A method according to claim 1 wherein identifying all of the F-wavelets contained within the plurality of F-wave traces comprises:
   using the identified waveform features of the F-wave traces to identify individual F-wave components within the plurality of F-wave traces; and
   decomposing each individual F-wave component so as to extract each constituent F-wavelet contained within that F-wave component.

3. A method for identifying each of the constituent F-wavelets contained within a plurality F-wave traces, wherein the plurality of F-wave traces are created as a result of electrical stimulation of a nerve in a patient, the method comprising the steps of using a computer to:
   identify specific waveform features of the plurality of F-wave traces;
   identify F-wave components within the plurality of F-wave traces, wherein the F-wave components comprise activity regions separated by quiet regions;
   for each F-wave component identified within the plurality of F-wave traces, compare the F-wave component with at least one F-wave component of at least one other F-wave trace and calculate a similarity measurement for that F-wave component;
   for each F-wave component having a similarity measurement which does not meet a pre-determined criteria, define the F-wave component as constituting a single F-wavelet, and for each F-wave component having a similarity measurement which meets the pre-determined criteria, define the F-wave component as constituting more than one F-wavelet; and for each F-wave component defined to constitute more than one F-wavelet, decompose that F-wave component into the constituent F-wavelets of that F-wave component based on the similarity measurement for that F-wave component.

4. A method according to claim 3 wherein the specific waveform features identified within the plurality of F-wave traces comprise at least two selected from the group consisting of: onset; amplitude; end; and duration.

5. A method according to claim 3 wherein calculating the similarity measurement for that F-wave component comprises one selected from the group consisting of: the Normalized Cross-Correlation (NCC) method; the Pseudo-correlation (PsC) method; and the Normalized Euclidian Distance (NED) method.

6. A method according to claim 3 wherein decomposing the F-wave component into the constituent F-wavelets of that F-wave component comprises:
   (1) determining whether the F-wave component is identical to the superimposition of two existing F-wave components within other F-wave traces and, if the F-wave component is identical to the superimposition of two existing F-wave components within other F-wave traces, decomposing that F-wave component into the two existing F-wave components from the other F-wave traces;
   (2) determining whether the F-wave component has a portion similar to an existing F-wave component within another F-wave trace and, if the F-wave component has a portion similar to an existing F-wave component within another F-wave trace, subtracting the existing F-wave component from the F-wave component which is to be decomposed, so as to yield a residual F-wave component, and if an onset or end point of the residual F-wave component has shifted, decomposing the F-wave component which is to be decomposed into the existing F-wave component and the residual F-wave component; and
   applying steps (1) and (2) recursively until all decomposition has been effected, and then defining each of the resulting F-wave components as an F-wavelet.

7. A method according to claim 3 wherein F-wave component decomposition is conducted in a transform domain, and further wherein the transform domain is the frequency domain.

8. A method for creating an F-wave TOA profile for a nerve, the method comprising the steps of using a computer to:
   (1) electrically stimulate the nerve so as to create a plurality of F-wave traces;
   (2) identify specific waveform features of the plurality of F-wave traces;
   (3) use the identified waveform features, to identify individual F-wave components within each of the plurality of F-wave traces, wherein the F-wave components comprise activity regions separated by quiet regions;
   (4) compare each F-wave component within a specific one of the plurality of F-wave traces with at least one F-wave component of at least one other F-wave trace and calculate a similarity measurement for each F-wave component;
   (5) for each F-wave component having a similarity measurement which does not meet a pre-determined criteria, define the F-wave component as constituting a single F-wavelet, and for each F-wave component having a similarity measurement which meets the pre-determined criteria, define the F-wave component as constituting more than one F-wavelet;
   (6) for each F-wave component examined and determined to constitute more than one F-wavelet, decompose that F-wave component into the constituent F-wavelets of that F-wave component;
   define each of the remaining F-wave components as an F-wavelet;
   estimate the time of arrival (TOA) of each F-wavelet contained within the specific F-wave trace; and
   create a TOA profile for the nerve using the estimated TOAs from the specific F-wave trace.

9. A method according to claim 8 wherein the specific waveform features identified within the plurality of F-wave traces comprise at least two selected from the group consisting of: onset; amplitude; end; and duration.

10. A method according to claim 8 wherein calculating the similarity measurement for that F-wave component comprises one selected from the group consisting of: the Normalized Cross-Correlation (NCC) method; the Pseudo-correlation (PsC) method; and the Normalized Euclidian Distance (NED) method.

11. A method according to claim 8 wherein decomposing that F-wave component into the constituent F-wavelets of that F-wave component comprises:
   (i) determining whether that F-wave component is identical to the superimposition of two existing F-wave components within other F-wave traces and, if so, decomposing that F-wave component into the two existing F-wave components from the other F-wave traces;
   (ii) determining whether that F-wave component has a portion similar to an existing F-wave component within another F-wave trace, and if so, subtracting the existing F-wave component from that F-wave component which is to be decomposed, so as to yield a residual F-wave component, and if the duration of the residual F-wave component is different than that F-wave component which is to be decomposed, decomposing that F-wave component into the existing F-wave component and the residual F-wave component; and
   applying steps (i) and (ii) recursively until all decomposition has been effected, and then defining each of the resulting F-wave components as an F-wavelet.

12. A method according to claim 8 wherein:
   an activity region is determined by first determining the noise level of the plurality of F-wave traces, and then defining the activity region as having an amplitude which exceeds the amplitude of the noise level by the pre-determined criteria; and
   a quiet region is defined as having an amplitude which does not exceed the amplitude of the noise level by the pre-determined criteria, and which has a segment length which is longer than some pre-determined criteria.

13. A method according to claim 8 wherein the plurality of F-wave traces are pre-processed so as to reduce at least one of: noise; power-line frequency interference (PFI); and baseline disturbances.

14. A method according to claim 8 wherein F-wave component decomposition is conducted in a transform domain, wherein the transform domain is the frequency domain and the estimated TOA of each F-wave component is estimated in another domain, and further wherein the other domain is the time domain.

15. A system for the assessment of neuromuscular function of an individual, the system comprising:
    a stimulator for stimulating a nerve so as to create a plurality of F-wave traces;
    a computer which is configured to:
        (i) identify specific waveform features of each of the plurality of F-wave traces;
        (ii) use the identified waveform features to identify all F-wavelets contained within the plurality of F-wave traces;
        (iii) estimate a time of arrival (TOA) for each F-wavelet contained within the plurality of F-wave traces;
        (iv) create a TOA profile for the nerve using the estimated TOA of each F-wavelet contained within the plurality of F-wave traces; and
        (v) use the TOA profile of the nerve to assess neuromuscular function of the individual.

16. The system according to claim 15 wherein the computer which is configured to identify all of the F-wavelets contained within the plurality of F-wave traces is further configured to:
    use the identified waveform features of each of the plurality of F-wave traces to identify individual F-wave components within the plurality of F-wave traces; and
    decompose each individual F-wave component so as to extract each constituent F-wavelet contained within that F-wave component.

17. A system for identifying each of the constituent F-wavelets contained within a plurality of F-wave traces, the system comprising:
    a stimulator for stimulating a nerve so as to create the plurality of F-wave traces;
    a computer which is configured to:
        (i) identify specific waveform features of the plurality of F-wave traces;
        (ii) identify F-wave components within the plurality of F-wave traces trace, wherein the F-wave components comprise activity regions separated by quiet regions;
        (iii) compare each of the F-wave components with at least one F-wave component of at least one other F-wave trace and calculate a similarity measurement for that F-wave component and,
            for each F-wave component having a similarity measurement which does not meet a pre-determined criteria, define the F-wave component as constituting a single F-wavelet, and for each F-wave component having a similarity measurement which meets the pre-determined criteria, define the F-wave component as constituting more than one F-wavelet and,
            for each F-wave component defined to constitute more than one F-wavelet, decompose that F-wave component into the constituent F-wavelets of that F-wave component based on the similarity measurement for that F-wave component.

18. The system according to claim 17 wherein the specific waveform features identified within the plurality of F-wave traces comprise at least two selected from the group consisting of: onset; amplitude; end; and duration.

19. The system according to claim 17 wherein calculating the similarity measurement for that F-wave component comprises one selected from the group consisting of: the Normalized Cross-Correlation (NCC) method; the Pseudo-correlation (PsC) method; and the Normalized Euclidian Distance (NED) method.

20. The system according to claim 17 wherein the computer which is configured to decompose the F-wave component into the constituent F-wavelets of each F-wave component is further configured to:
    (1) determine whether the F-wave component is identical to the superimposition of two existing F-wave components within other F-wave traces and, if the F-wave component is identical to the superimposition of two existing F-wave components within other F-wave traces, decompose that F-wave component into the two existing F-wave components from the other F-wave traces;
    (2) determine whether the F-wave component has a portion similar to an existing F-wave component within another F-wave trace and, if the F-wave component has a portion similar to an existing F-wave component within another F-wave trace, subtract the existing F-wave component from the F-wave component which is to be decomposed, so as to yield a residual F-wave component, and if an onset or end point of the residual F-wave component has shifted, decompose the F-wave component which is to be decomposed into the existing F-wave component and the residual F-wave component; and
    apply steps (1) and (2) recursively until all decomposition has been effected, and then define each of the resulting F-wave components as an F-wavelet.

21. The system according to claim 17 wherein the computer is further configured to conduct F-wave component decomposition in a transform domain, and further wherein the transform domain is the frequency domain.

22. A system for creating an F-wave TOA profile for a nerve, the system comprising:
    a stimulator for stimulating the nerve so as to create a plurality of F-wave traces;
    a computer which is configured to:
        (i) identify specific waveform features of each of the plurality of F-wave traces;
        (ii) use the identified waveform features to identify individual F-wave components within each of the plurality of F-wave traces, wherein the F-wave components comprise activity regions separated by quiet regions;
        (iii) compare each F-wave component within a specific one of the plurality of F-wave traces with at least one F-wave component of at least one other F-wave trace and calculate a similarity measurement for each F-wave component;
        (iv) define each F-wave component as constituting a single F-wavelet for each F-wave component having a similarity measurement which does not meet a pre-determined criteria, and as constituting more than one F-wavelet for each F-wave component having a similarity measurement which meets the pre-determined criteria,
        (v) decompose each F-wave component examined and determined to constitute more than one F-wavelet into the constituent F-wavelets of that F-wave component;
        (vi) define each of the remaining F-wave components as an F-wavelet;
        (vii) estimate the time of arrival (TOA) of each F-wavelet contained within the specific F-wave trace; and
        (viii) create a TOA profile for the nerve using the estimated TOAs from the specific F-wave trace.

23. The system according to claim 22 wherein the specific waveform features identified within the plurality of F-wave traces comprise at least two selected from the group consisting of: onset; amplitude; end; and duration.

24. The system according to claim 22 wherein calculating the similarity measurement for each F-wave component comprises one selected from the group consisting of: the Normalized Cross-Correlation (NCC) method; the Pseudo-correlation (PsC) method; and the Normalized Euclidian Distance (NED) method.

25. The system according to claim 22 wherein the computer which is configured to decompose each F-wave component examined and determined to constitute more than one F-wavelet into the constituent F-wavelets of that F-wave component is further configured to:
   (1) determine whether that F-wave component is identical to the superimposition of two existing F-wave components within other F-wave traces and, if so, decompose that F-wave component into the two existing F-wave components from the other F-wave traces;
   (2) determine whether that F-wave component has a portion similar to an existing F-wave component within another F-wave trace, and if so, subtract the existing F-wave component from that F-wave component which is to be decomposed, so as to yield a residual F-wave component, and if the duration of the residual F-wave component is different than that F-wave component which is to be decomposed, decompose that F-wave component into the existing F-wave component and the residual F-wave component; and
   apply steps (1) and (2) recursively until all decomposition has been effected, and then define each of the resulting F-wave components as an F-wavelet.

26. The system according to claim 22 wherein the computer is further configured to:
   determine an activity region by first determining the noise level of the plurality of F-wave traces, and then defining the activity region as having an amplitude which exceeds the amplitude of the noise level by the pre-determined criteria; and
   define a quiet region as having an amplitude which does not exceed the amplitude of the noise level by the pre-determined criteria, and which has a segment length which is longer than some pre-determined criteria.

27. The system according to claim 22 wherein the plurality of F-wave traces are pre-processed so as to reduce at least one of: noise; power-line frequency interference (PFI); and baseline disturbances.

28. The system according to claim 22 wherein the computer is further configured to conduct F-wave component decomposition in a transform domain, wherein the transform domain is the frequency domain, and the computer is further configured to estimate the TOA of each F-wave component in another domain, and further wherein the other domain is the time domain.

29. A method for the assessment of neuromuscular function of a person, the method comprising the steps of using a computer to:
   electrically stimulate a nerve so as to create a plurality of F-wave traces;
   identify specific waveform features of each of the plurality of F-wave traces;
   use the identified waveform features to identify all F-wave components contained within the plurality of F-wave traces;
   estimate a time of arrival (TOA) for each F-wave component contained within the plurality of F-wave traces;
   create a TOA profile for the person's nerve using the estimated TOA of each F-wave component contained within the plurality of F-wave traces; and
   use the TOA profile of the person's nerve to assess neuromuscular function of the person.

30. A method for identifying each of the constituent F-wavelets contained within a plurality of F-wave traces, wherein the plurality of F-wave traces are created as a result of electrical stimulation of a nerve in a patient, the method comprising the steps of using a computer to:
   identify specific waveform features of the plurality of F-wave traces;
   identify F-wave components within the plurality of F-wave traces, wherein the F-wave components comprise activity regions separated by quiet regions;
   for each F-wave component identified from the plurality of F-wave traces, compare that F-wave component with at least one F-wave component of at least one other F-wave trace and calculate a similarity measurement for that F-wave component with respect to the at least one compared F-wave component;
   for each F-wave component having a similarity measurement which does not meet a pre-determined criteria, define the F-wave component as constituting a single F-wavelet, and for each F-wave component having a similarity measurement which meets the pre-determined criteria, examine the F-wave component as if constituting more than one F-wavelet; and
   for each F-wave component verified to constitute more than one F-wavelet, decompose that F-wave component into the constituent F-wavelets of that F-wave component so as to identify each of the constituent F-wavelets contained within the F-wave trace.

31. A method for creating an F-wave TOA profile for a person's nerve, the method comprising the steps of using a computer to:
   (1) electrically stimulate the nerve so as to create a plurality of F-wave traces;
   (2) identify specific waveform features of each of the plurality of F-wave traces;
   (3) using the identified waveform features, identify individual F-wave components within the plurality of F-wave traces, wherein the F-wave components comprise activity regions separated by quiet regions;
   (4) compare each F-wave component within a specific one of the plurality of F-wave traces with at least one F-wave component of at least one other F-wave trace and calculate a similarity measurement for each F-wave component;
   (5) for each F-wave component having a similarity measurement which does not meet a pre-determined criteria, define the F-wave component as constituting a single F-wavelet; and for each F-wave component having a similarity measurement which meets the pre-determined criteria, examine the F-wave component as if constituting more than one F-wavelet;
   (6) for each F-wave component examined to constitute more than one F-wavelet, decompose that F-wave component into the constituent F-wavelets of that F-wave component;
   (7) treat each extracted F-wavelet as a new F-wave component, and apply steps (4) through (6) recursively until all decomposition has been effected;
   estimate the time of arrival (TOA) of each F-wavelet contained within the specific F-wave trace; and
   create a TOA profile for the person's nerve using the estimated TOAs.

* * * * *